(12) United States Patent
Sonek (10) Patent No.: US 7,022,082 B2
(45) Date of Patent: Apr. 4, 2006

(54) NEEDLE GUIDE SYSTEMS AND METHODS

(76) Inventor: Jiri D. Sonek, 540 Rustic Trail, Beavercreek, OH (US) 45434

( * ) Notice: Subject to any disclaimer, the term of this patent is extended or adjusted under 35 U.S.C. 154(b) by 0 days.

(21) Appl. No.: 10/144,372

(22) Filed: May 13, 2002

(65) Prior Publication Data

US 2003/0212414 A1    Nov. 13, 2003

(51) Int. Cl.
*A61B 19/00* (2006.01)
(52) U.S. Cl. .................. 600/461; 606/130; 600/417
(58) Field of Classification Search ............ 606/130; 600/417, 461; 604/116
See application file for complete search history.

(56) References Cited

U.S. PATENT DOCUMENTS

| 4,899,756 | A | 2/1990 | Sonek |
| 5,052,396 | A | 10/1991 | Wedel et al. |
| 5,235,987 | A | 8/1993 | Wolfe |
| 5,623,931 | A | 4/1997 | Wung et al. |
| 5,647,373 | A | 7/1997 | Paltieli |
| 5,758,650 | A | 6/1998 | Miller et al. |
| 5,855,558 | A | 1/1999 | Nakao et al. |
| 5,924,992 | A | 7/1999 | Park et al. |
| 5,941,889 | A | 8/1999 | Cermak |
| 6,203,499 | B1 | 3/2001 | Imling et al. |
| 6,216,029 | B1 | 4/2001 | Paltieli |
| 6,485,426 | B1 * | 11/2002 | Sandhu ................ 600/461 |

* cited by examiner

*Primary Examiner*—Michael Thaler
(74) *Attorney, Agent, or Firm*—Dinsmore & Shohl LLP (57) ABSTRACT

A needle guide system comprises a base adapted for non-pivotal connection to an imaging device, an arm pivotally connected to the base, and a needle guide pivotally connected to the arm at a point distal from the arm-base connection. The needle guide is adapted to receive at least one needle. The length of the arm extending between the base and the needle guide is adjustable. Methods for positioning a needle relative to an imaging device employ the needle guide system.

30 Claims, 6 Drawing Sheets

NEEDLE GUIDE SYSTEMS AND METHODS

FIELD OF THE INVENTION

The present invention relates to medical devices and more particularly to needle guide systems and methods for positioning a needle relative to an imaging device.

BACKGROUND OF THE INVENTION

Imaging devices provide images which assist medical practitioners in positioning a needle to perform a wide range of procedures. These include such procedures as drainage, precision injections, biopsies, and ultrasonic imaging in performing, for example, amniocentesis, cordocentesis and transabdominal chorionic villus sampling.

While relatively broad, the imaging beam of such imaging devices is generally flat. To obtain a clear image of a needle as it is guided into a desired target area, it is often desirable for the needle to be positioned at an angle of approximately 45 degrees with respect to an axis of an imaging beam. However, it has often been difficult to maintain a needle within an imaging beam, particularly within the desired angle with respect to the imaging beam axis. Once the needle escapes this axis, it will not be seen by the imaging device, which may result in an inaccurate tissue sample or require reinsertion of the needle.

Various attempts have been made in the past to assist medical practitioners in maintaining a needle within an imaging beam axis. U.S. Pat. No. 5,758,650 issued Jun. 2, 1998 to Miller et al and U.S. Pat. No. 5,941,889 issued Aug. 24, 1999 to Cermak disclose needle guiding apparatuses adapted for attachment to a probe or transducer of an imaging device. While these devices provided some movement of the needle relative to the imaging device, such movement is severely limited. For example, to obtain a suitable entrant angle for the needle, the angle of the imaging device relative to the desired target area is severely restricted. As a result, the medical practitioner remains limited in properly positioning the needle prior to and during insertion, as well as properly positioning the imaging device once the needle is inserted into the desired target area.

U.S. Pat. No. 4,899,756 to Sonek discloses an articulated needle guide which is advantages for facilitating needle positioning during ultrasound imaging, yet further flexibility may be desired.

Accordingly, there is a continuing need for needle guide systems that allow proper positioning of a needle prior to and during insertion, while also allowing independent positioning of an imaging device with respect to the needle guide system once a needle is inserted into a desired target area. There is also a continuing need for methods for positioning a needle relative to an imaging device.

SUMMARY OF THE INVENTION

Accordingly, it is an object of the present invention to provide improved needle guide systems which allow proper positioning of a needle with respect to an imaging beam axis of an imaging device.

It is a further object of the present invention to provide improved needle guide systems which allow independent positioning of an imaging device with respect to a needle guide system, before, during or after needle insertion into the body.

It is still a further object of the present invention to provide improved methods for positioning a needle relative to an imaging device.

In one embodiment, the invention is directed to needle guide systems comprising a base adapted for non-pivotal connection to an imaging device, an arm pivotally connected to the base, and a needle guide pivotally connected to the arm at a point distal from the arm-base connection. The needle guide is adapted to receive at least one needle, and the length of the arm extending between the base and the needle guide is adjustable.

In accordance with an additional embodiment of the present invention, needle guide systems comprise a base adapted for non-pivotal connection to an imaging device, a connector adapted to removably secure the base to an imaging device, an arm pivotally connected to the base, and a needle guide pivotally connected to the arm at a point distal from the arm-base connection. The needle guide is adapted to receive at least one needle, and the length of the arm extending between the base and the needle guide is adjustable. The arm and the needle guide are positionable at a predetermined angle with respect to an imaging beam axis of an imaging device.

In accordance with yet another embodiment of the present invention, methods are provided for positioning a needle relative to an imaging device. The methods comprise attaching a needle guide system to an imaging device at a desired attachment location. The needle guide system comprises a base adapted for non-pivotal connection to an imaging device, a connector adapted to removably secure the base to an imaging device, an arm pivotally connected to the base, and a needle guide pivotally connected to the arm at a point distal from the arm-base connection. The needle guide is adapted to receive at least one needle, and the length of the arm extending between the base and the needle guide is adjustable. The imaging device has an imaging beam axis. The methods further comprise positioning the imaging device on a body surface to provide an image of a desired target area of a body; pivoting the arm and/or the needle guide relative to the body surface, wherein the needle guide and arm are aligned in a predetermined orientation with respect to the imaging beam axis; and inserting a needle through the needle guide to contact the desired target area.

The needle guide systems and the methods of the invention are advantageous in facilitating proper positioning of a needle with respect to an imaging beam axis of an imaging device. Still other objects and advantages of the present invention will become apparent to those skilled in the art from the following detailed description where alternative exemplary embodiments of this invention are shown and described. As will be realized, the invention is capable of other different, obvious aspects and embodiments, all without departing from the invention. Accordingly, the drawings and descriptions should be regarded as illustrative in nature and not as restrictive.

BRIEF DESCRIPTION OF THE DRAWINGS

While the specification concludes with claims which particularly point out and distinctly claim the present invention, it is believed that the present invention will be better understood from the following detailed description of specific embodiments taken in conjunction with the accompanying drawings in which;

DETAILED DESCRIPTION

As indicated in the drawings, the present invention is directed to needle guide systems. Advantageously, the needle guide system of the present invention is adapted to properly position a needle within a narrow imaging beam of an imaging device. In one embodiment, the needle guide system allows such proper positioning while maintaining independent adjustment of the imaging device relative to the needle guide system. Methods in accordance with the present invention are directed to positioning a needle relative to an imaging device.

As used herein, "body" is intended to refer to an individual on whom a procedure is performed. As used herein, "individual" is intended to refer to animals, including but not limited to humans, mammals, and rodents. As used herein, "predetermined orientation" is intended to refer to a position or alignment of the arm and/or needle guide with respect to an imaging device before, during, or after a needle is inserted into the body. As used herein, "desired target area" is intended to refer to the preferred location in the body into which a needle is to be inserted. As used herein, "imaging device" is intended to refer to any imaging device which emits radiation or sound waves to a desired target area. In one embodiment, the imaging device may be ultrasonic; however, in further embodiments the imaging device may be X-ray imaging, magnetic resonance imaging (MRI), or combinations thereof.

Referring now to the drawing figures in detail, where like numerals indicate the same elements throughout the views, FIGS. 1–3 and 9–10 illustrate a needle guide system 44 in accordance with one embodiment of the invention. The needle guide system 44 comprises a base 24 adapted to be non-pivotally connected to an imaging device, shown generally at 20 in FIGS. 1 and 10. The system further comprises an arm 26 pivotally connected to the base 24 at an arm-base connection 54, and a needle guide 30 pivotally connected to the arm 26 at a point distal from the arm-base connection 54. The needle guide 30 is adaptable to receive at least one needle, shown at 32 in FIGS. 1 and 10, and, as will be described in further detail below, the length of the arm 26 extending between the base 24 and the needle guide 30 is adjustable. One skilled in he art will appreciate that the needle guide system may be formed of any material, which includes, but is not limited to, synthetic resin, stainless steel or other strong, stain, corrosion-resistant, nonmagnetic metal. Further, one skilled in the art will appreciate that the needle guide system and any element therein may be provided as a sterile disposable item.

Figure 5:
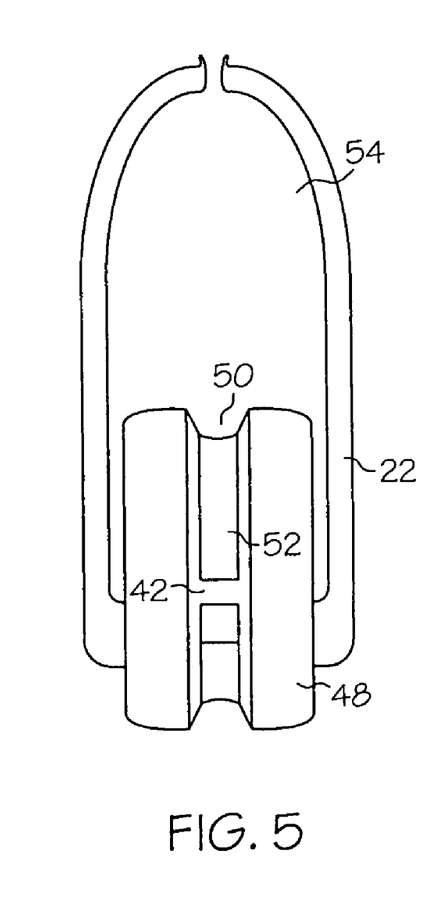
FIG. 5 is a top plane view of the base of the needle guide system of FIG. 1 including a connector adapted to removably secure a base to an imaging device.
Figure 9:
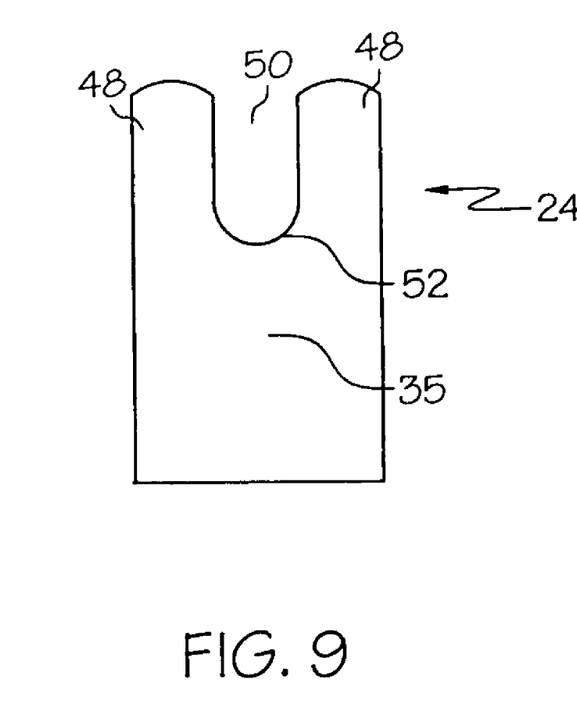
FIG. 9 is an end view of a base of the needle guide system of FIG. 1 illustrating a mounting base surface.

The exemplary base 24, illustrated in further detail in FIGS. 5 and 9, includes two base sidewalls 48 equal to one another in width and length and is provided with a longitudinally extending base slot 50 between the base sidewalls 48. The base 24 also includes a base pin 42 arranged in the longitudinally extending base slot 50 and extending between and connected to the base sidewalls 48. The base 24 is adapted to allow the arm 26, illustrated in more detail in FIG. 6, to pivot around the base pin 42 and to slide in the longitudinally extending base slot 50. One skilled in the art will appreciate that the base of the needle guide system of the present invention may comprise various alternate structures which provide a pivotal and sliding connection as described herein.

In one embodiment in accordance with the present invention, the base may comprise a backstop which limits the extent of pivot motion when a predetermined length of the arm is received in the base slot. For example, with reference to FIGS. 5 and 9, the base 24 may include a backstop 52 which limits the extent of pivot motion of the arm 26 when a length of the arm equal to the base slot is received in the base slot 50.

Figure 1:
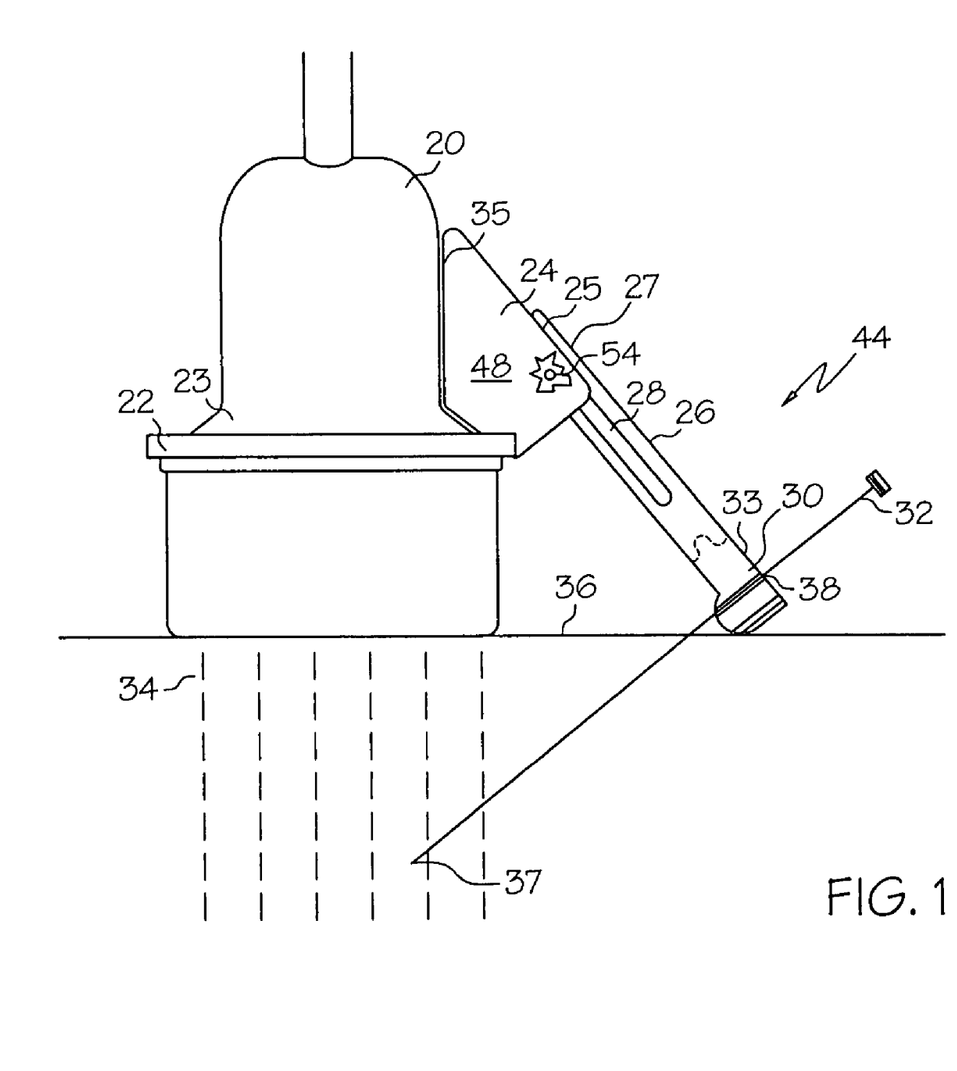
FIG. 1 is a side elevational view of one embodiment of a needle guide system according to the invention in combination with an imaging device.
Figure 2:
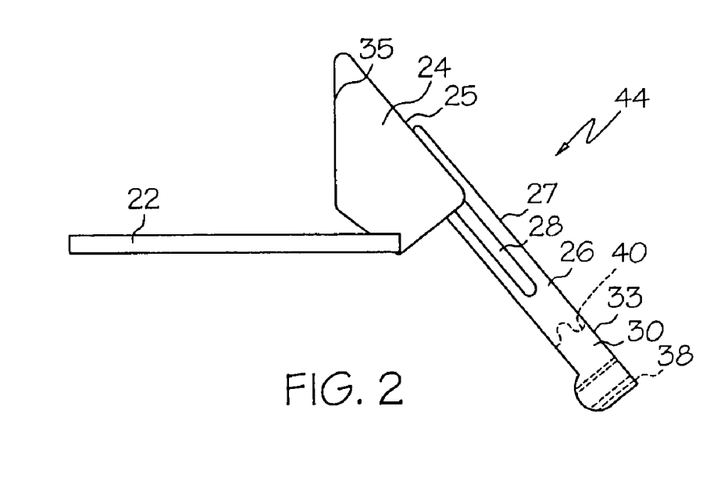
FIG. 2 is a side elevational view of the needle guide system of FIG. 1.
Figure 3:
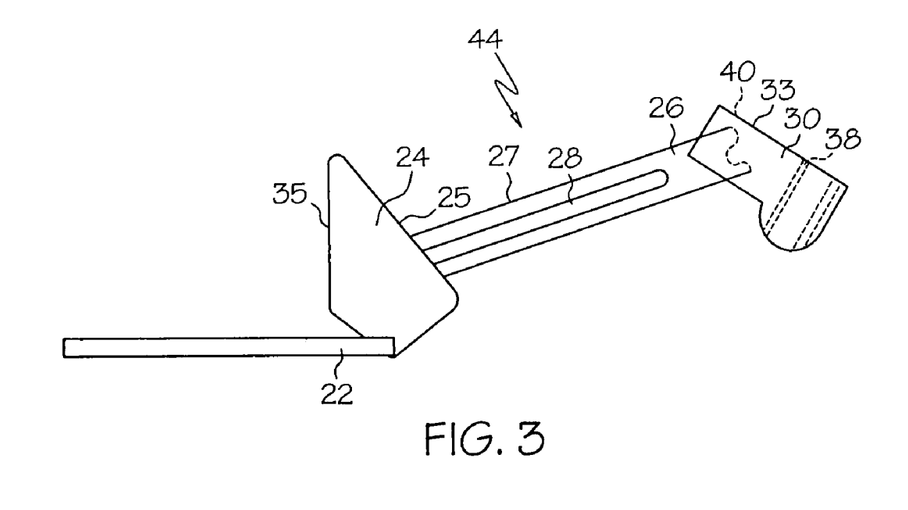
FIG. 3 is a side elevational view of the needle guide system of FIG. 1 illustrating pivotal connections provided by a base and a needle guide with respect to an arm.
Figure 4:
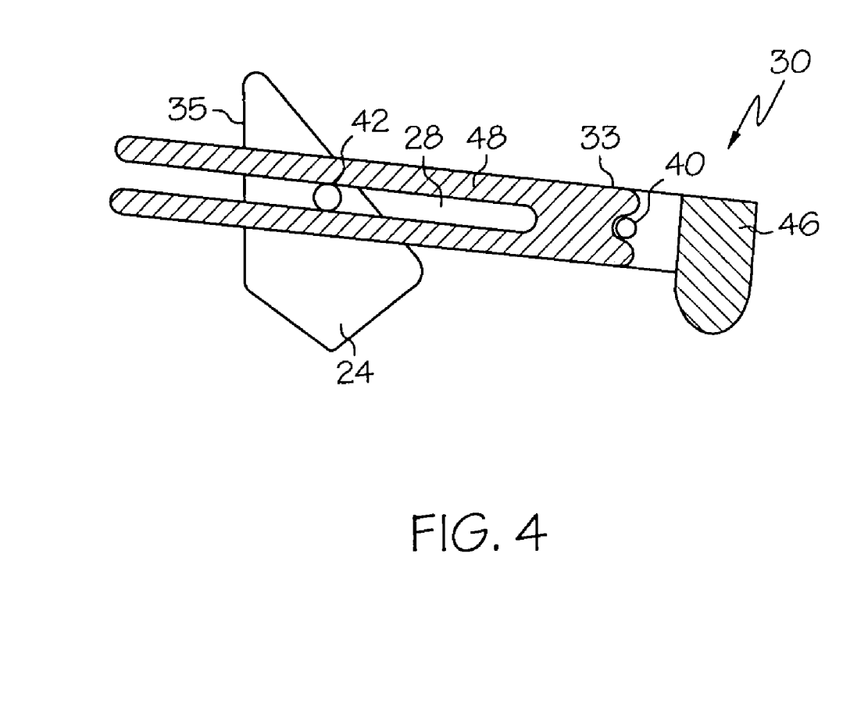
FIG. 4 is a cross sectional view of the needle guide system of FIG. 1 taken along the length of an arm.
Figure 6:
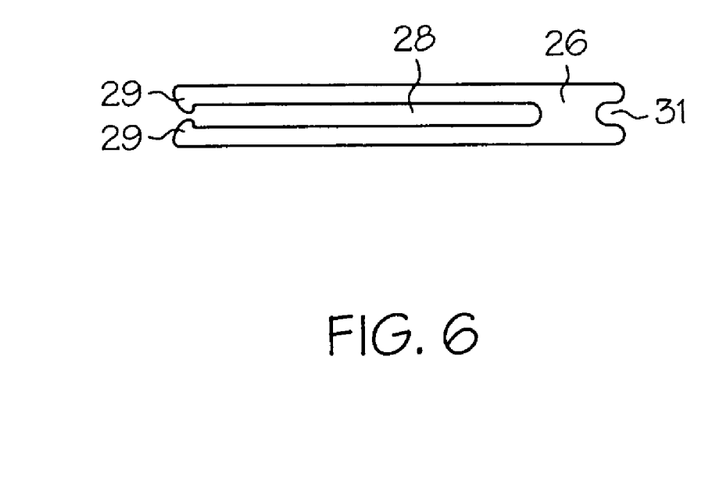
FIG. 6 is a side elevational view of an arm included in the needle guide system of FIG. 1.
Figure 10:
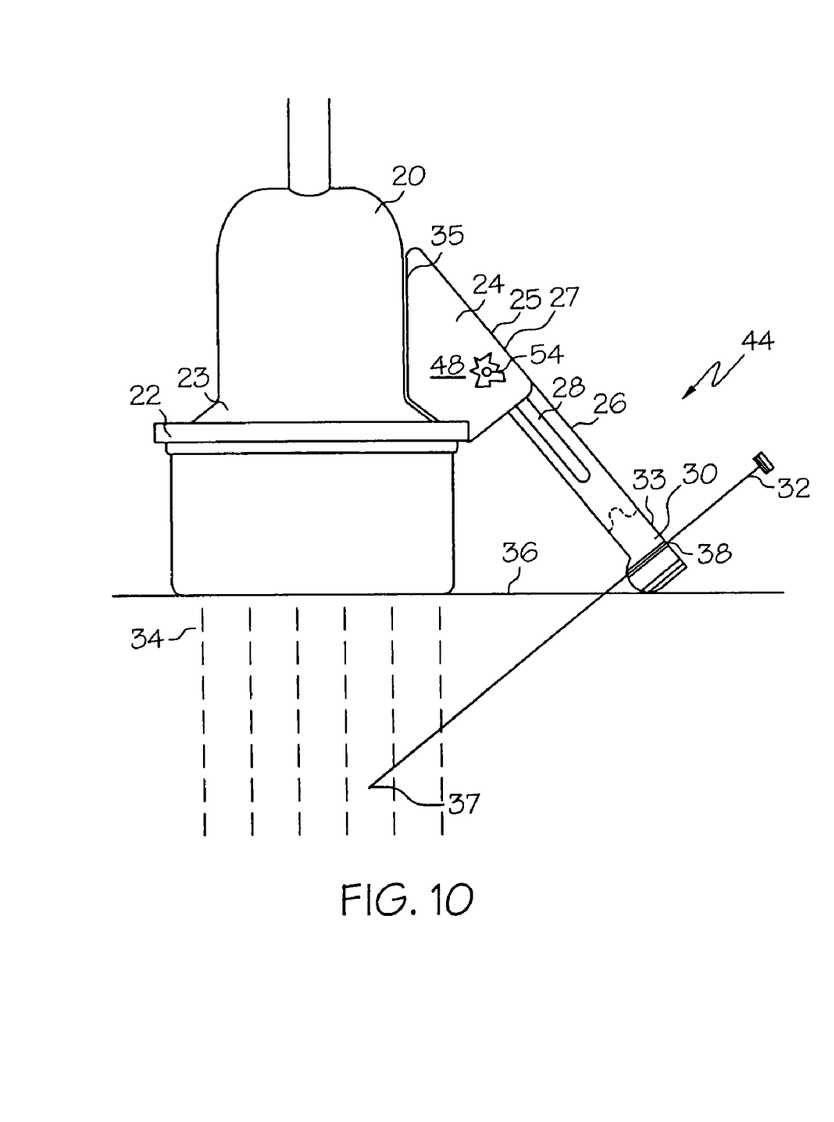
FIG. 10 is a side elevational view of one embodiment of a needle guide system according to the invention in combination with an imaging device.
Figure 11:
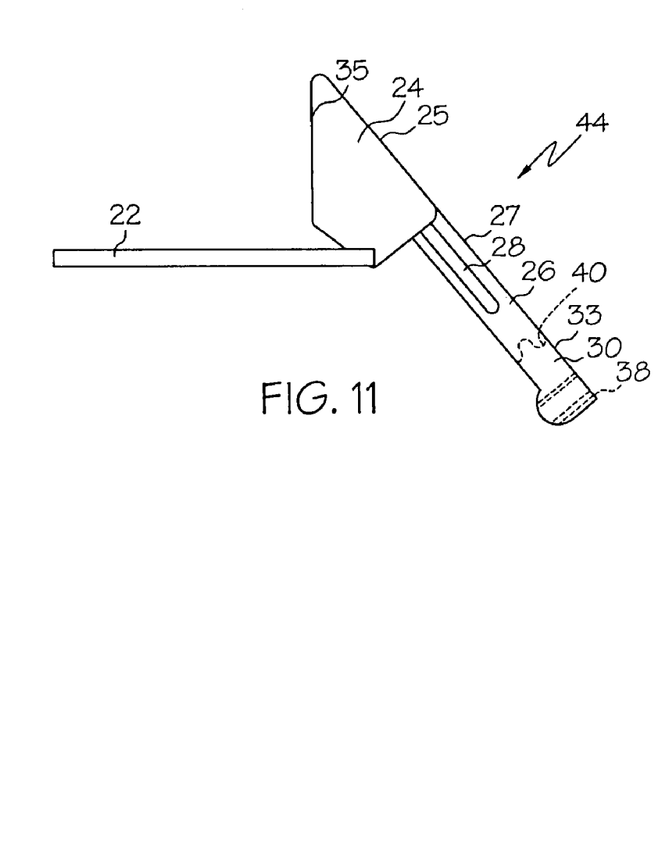
FIG. 11 is a side elevational view of the needle guide system of FIG. 10.

The exemplary arm 26, as illustrated in FIGS. 1, 6 and 10, is provided with a longitudinally extending arm slot 28 and a needle guide socket 31. The needle guide socket 31 is located at a point distal from the arm-base connection 54 and, in turn, from the longitudinally extending arm slot 28 as the arm slot 28 allows the arm 26 to be pivotally connected to the base 24. The arm slot 28 further allows the length of the arm 26 extending between the base 24 and the needle guide 30 to be adjusted. The needle guide socket 31 is adapted to provide the arm 26 with a pivotal connection to the needle guide 30. One skilled in the art will appreciate that the arm of exemplary embodiments of the present invention may comprise various alternate structures which provide a pivotal and length-adjustable connection to the base and a pivotal connection to the needle guide.

As illustrated in FIG. 6, the exemplary embodiment of arm 26 in accordance with the present invention includes two protrusions 29, which act as stops adapted to prevent the base pin 42 from unintentional release from the longitudinally extending arm slot 28 until desired, for example when imaging has been completed and cleaning and storage of the needle guide system is desired. One skilled in the art will appreciate that the protrusions may comprise various designs to enable the protrusions to act as stops. Thus, in one embodiment, these protrusions allow the arm to be removably connected to the base. In yet a further embodiment, the arm of the exemplary embodiments of the present invention may comprise various alternate structures designed to provide a detachable and pivotal connection of the arm to the base.

Figure 7:
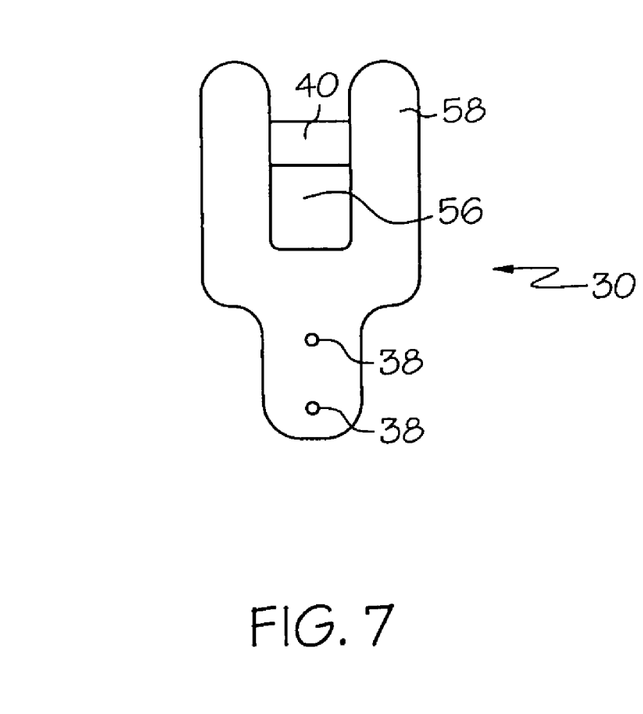
FIG. 7 is a top plane view of a needle guide included in the needle guide system of FIG. 1.
Figure 8:
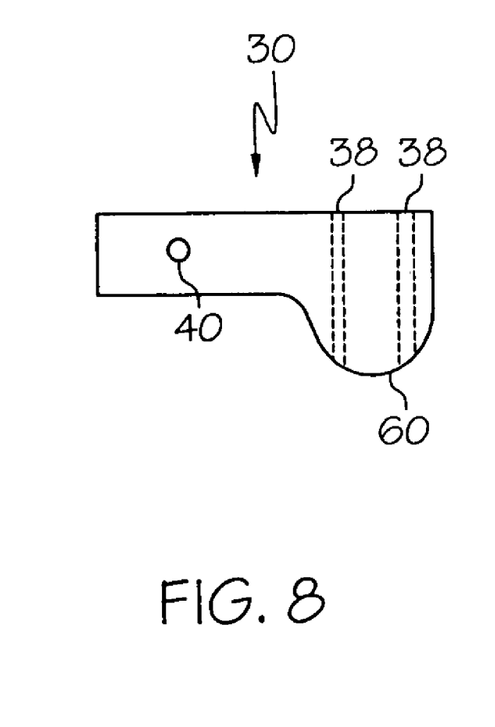
FIG. 8 is a side elevational view of the needle guide of FIG. 1 illustrating an arcuate surface of the needle guide.

The exemplary needle guide 30, as illustrated in FIGS. 7 and 8, is defined to be generally Y-shaped, wherein a needle guide pin 40 is provided in a U-shaped slot 56 of the needle guide 30. Needle guide sidewalls 58 surround the U-shaped slot 56 and are generally equal in length and width. In one embodiment, the needle guide pin 40 is received in the socket 31 of the arm 26 to pivotally connect the arm 26 to the needle guide 30. One skilled in the art will appreciate that the needle guide of the exemplary embodiments of the present invention may comprise various alternate structures designed to provide a pivotal connection with respect to the arm.

The needle guide 30 is also adapted to receive at least one needle, by providing the needle guide 30 with at least one guide hole 38. The needle guide of the exemplary embodiments of the present invention may comprise various alternate structures designed to provide guide holes. For example, as illustrated in FIGS. 7 and 8, multiple guide holes may be provided to allow for a plurality of needle sizes. In another exemplary embodiment, the needle guide 30, as demonstrated in FIG. 8, may comprise an arcuate surface 60, which permits ease of adjustment and comfortable contact with a body surface of a desired target area. In yet a further embodiment, as the needle guide 30 may be removably connected to the arm 26, one skilled in the art will appreciate that the needle guide 30 may be provided as a sterile disposable item in a package, together with or separately from a disposable sterile needle.

In the embodiment of FIGS. 1, and 5 and 10, as well as in other embodiments of the present invention, the needle guide system may comprise a connector 22 to removably secure the base 24 of the needle guide system 44 to an imaging device, shown generally at 20 in FIGS. 1 and 10. A non-pivotal connection of the base to the imaging device is preferred. One skilled in the art will appreciate that the connector may have different configurations as required by the design of the imaging device and/or base of the needle guide system. Also, one skilled in the art will appreciate that the connector may be formed of any material, and suitably may be formed of a material which allows the connector to adjustably and/or removably secure the base to an imaging device. The connector may be, for example, but is not limited to, a stainless steel, Velcro, cloth, or elastic strap or band, or may comprise combinations thereof.

Additionally, the base 24 in the exemplary embodiment of FIGS. 1, 9 and 10 in accordance with the present invention comprises a base-mounting surface 35 which is adapted for positioning flush with respect to the adjacent surface of an imaging device. In addition, the base-mounting surface 35 may be designed to be adaptable for a plurality of shapes or sizes of an imaging device, for example, by including a soft layer of foam material or the like on the surface.

As the needle guide system has been shown to be pivotable and adjustable, the needle guide system is adaptable to properly position a needle for penetration into an imaging beam of an imaging device. In specific embodiments, the needle guide system is particularly advantageous for positioning a needle at a predetermined orientation with respect to an imaging device. In further embodiments, the needle guide system is advantageous for positioning a needle at a predetermined angle with respect to an axis of an imaging beam. While the needle guide system may be employed to position the needle at an angle of from about 10° to about 80° or more with respect to an imaging beam axis, it is often suitable to position the needle at an angle of about 45° with respect to the imaging beam axis.

As exemplified in FIGS. 1, 2, 4, and 10–11, the exemplary needle guide system 44 is adapted to be adjustable to a predetermined orientation. The base, arm and/or needle guide of the systems of the present invention may comprise various structures to achieve the predetermined orientation. In exemplary embodiments, alignment arrangements are provided. For example, in one embodiment, the arm 26 includes an arm alignment surface 27 and the base 24 includes a base alignment surface 25, wherein the arm alignment surface 27 may be arranged parallel with the base alignment surface 25 to provide a predetermined desired orientation of a needle. In further embodiments, the needle guide 30 is provided with a needle guide alignment surface 33 which may be adjusted to a position at which the needle guide alignment surface 33 is parallel with the arm alignment surface 27 to provide a predetermined orientation of a needle. In yet another embodiment, the adjacent, any two or all three, alignment surfaces may be coplanar, i.e., extend along the same plane. In yet a further embodiment, the arm alignment surface 27 and the base alignment surface 25 may be parallel while the arm alignment surface 27 and needle guide alignment surface 33 are coplanar. In a further embodiment, the arm alignment surface 27 and the base alignment surface 25 may be coplanar while the arm alignment surface 27 and needle guide alignment surface 33 are parallel. When aligned in the predetermined orientation, a needle may be inserted to contact the desired target area. In an exemplary embodiment of the present invention, as illustrated in FIGS. 1 and 10, the needle 32 is inserted through a guide hole 38 at an angle for obtaining a clear image of the needle 32 on the viewing device as it is guided into the desired target area 37. For example, in one embodiment, the needle 37 is inserted at an angle of about 45 degrees with respect to the surface of the body 36 into the desired target area 37, and at an angle of about 45° with respect to the imaging beam axis. In another embodiment, the base alignment surface 25 is at an angle of about 45° with respect to the imaging beam axis.

In accordance with an exemplary embodiment of the present invention, as illustrated in FIGS. 1–10, the needle guide system may be operated and used in the following manner for positioning a needle relative to an imaging device. The needle guide system 44 is removably connected to an imaging device 20 by a connector 22. The imaging device 20 is then positioned to provide an image of a desired target area 37. The arm 26 and/or the needle guide 30 are then adjusted to a predetermined orientation, which may comprise aligning their respective alignment surfaces to position a needle in the needle guide 30 at a predetermined orientation with the axis of the imaging beam 34 of the imaging device 20, for example at an angle of about 45° A needle 32 is then inserted through a guide hole 38 provided by the needle guide 30 to contact the desired target area 37.

The method of the exemplary embodiments of the present invention may comprise various steps for positioning a needle relative to an imaging device. For example, the exemplary embodiments in accordance with the present invention may comprise repositioning the imaging device to obtain a second image of the desired target area. In yet a further exemplary embodiment, a second needle may be inserted before or after the insertion of a primary needle 32 into the desired target area 37.

Thus, it may be seen that the present needle guide system provides a substantial range of movement for orientating a needle without losing the image of the needle in the imaging beam axis of the imaging device.

The foregoing description of the various embodiments of the invention has been presented for the purposes of illustration and description. It is not intended to be exhaustive or to limit the invention to the precise form disclosed. Many alternatives, modifications and variations will be apparent to those skilled in the art of the above teaching. Accordingly, this invention is intended to embrace all alternatives, modifications and variations that have been discussed herein, and others that fall within the spirit and broad scope of the claims.

What is claimed is:

1. A needle guide system, comprising
   (a) a base adapted for non-pivotal connection to an imaging device, wherein the entire base cannot pivot with respect to an imaging device when it is non-pivotally connected thereto and wherein the base comprises a base alignment surface,
   (b) a single arm directly pivotally connected to the base at a connecting portion of the single arm, wherein the arm comprises an arm alignment surface and the arm is pivotable to a position at which the arm alignment surface is coplanar with the base alignment surface, and wherein the base alignment surface is adapted to position the arm at a predetermined orientation with respect to an imaging device, and
   (c) a needle guide pivotally connected to the single arm at a point distal from the connecting portion, wherein the needle guide is adapted to receive at least one needle and comprises a needle guide alignment surface and the needle guide is pivotable to a position at which the needle guide alignment surface is coplanar with the arm alignment surface,
   wherein the length of the single arm extending between the base and the needle guide is adjustable and wherein the single arm is rigid along the length extending between the base and the distal point such that the distal point is not pivotal with respect to the connecting portion.

2. The needle guide system according to claim 1, wherein the length of the arm extending between the arm-base connection and the needle guide is adjustable.

3. The needle guide system according to claim 1, further comprising a connector adapted to secure the base to an imaging device.

4. The needle guide system according to claim 3, wherein the connector is adapted to removably secure the base to an imaging device.

5. The needle guide system according to claim 3, wherein the connector is adjustable to secure the base to imaging devices having a plurality of shapes or sizes.

6. The needle guide system according to claim 1, wherein the base alignment surface is adapted to position the arm at a predetermined angle with respect to an imaging beam axis of an imaging device.

7. The needle guide system according to claim 1, wherein the arm is removably connected to the base.

8. The needle guide system according to claim 1, wherein the needle guide is removably connected to the arm.

9. The needle guide system according to claim 1, wherein the needle guide is provided with at least one guide hole adapted to receive a needle.

10. The needle guide system according to claim 9, wherein the needle guide is provided with a plurality of guide holes adapted to receive needles of different sizes.

11. The needle guide system according to claim 1, wherein the arm is provided with a longitudinally extending arm slot.

12. The needle guide system according to claim 11, wherein the base comprises a base pin arranged in the slot, and wherein the arm is adapted to pivot and slide with respect to the base.

13. The needle guide system according to claim 12, wherein the base pin is arranged in a longitudinal slot formed between two base walls of the base.

14. The needle guide system according to claim 1, wherein the needle guide comprises a needle guide pin, and wherein the arm is adapted to pivot on the pin.

15. A method for positioning a needle relative to an imaging device, the method comprising the steps of:
   a. attaching the needle guide system according to claim 1 to an imaging device at a desired attachment location;
   b. positioning the imaging device on a body surface to provide an image of a desired target area of a body;
   c. pivoting the single arm and/or the needle guide relative to the body surface wherein the needle guide alignment surface, the arm alignment surface and the base alignment surface are aligned to present a needle at a predetermined orientation with respect to the imaging beam axis; and
   d. inserting a needle through the needle guide to contact the desired target area.

16. The method according to claim 15, wherein the method further comprises repositioning the imaging device to obtain a second image of the desired target area.

17. The method according to claim 15, comprising pivoting the arm to a position at which the arm alignment surface is parallel with the base alignment surface.

18. The method according to claim 15, comprising pivoting the arm to a position at which the arm alignment surface is coplanar with the base alignment surface.

19. The method according to claim 17, comprising pivoting the needle guide to a position at which the needle guide alignment surface is parallel with the arm alignment surface.

20. The method according to claim 15, comprising pivoting the needle guide and the arm to respective positions at which the needle guide alignment surface, the arm alignment surface and the base alignment surface are coplanar.

21. A needle guide system, comprising
   (a) a base adapted for non-pivotal connection to an imaging device, wherein the base comprises a base alignment surface,
   (b) a connector adapted to removably secure the base to an imaging device such that the entire base cannot pivot with respect to an imaging device when it is non-pivotally connected thereto by the connector,
   (c) a single arm directly pivotally connected to the base at a connecting portion of the single arm, wherein the arm comprises an arm alignment surface and the arm is pivotable to a position at which the arm alignment surface is coplanar with the base alignment surface, and wherein the base alignment surface is adapted to position the arm at a predetermined angle with respect to an imaging beam axis of an imaging device, and
   (d) a needle guide pivotally connected to the single arm at a point distal from the connecting portion, wherein the needle guide is provided with at least one guide hole adapted to receive at least one needle and comprises a needle guide alignment surface and the needle guide is pivotable to a position at which the needle guide alignment surface is coplanar with the arm alignment surface,
   wherein the length of the single arm extending between the base and the needle guide is adjustable and wherein the single arm is rigid along the length extending between the base and the distal point such that the distal point is not pivotal with respect to the connecting portion.

22. The needle guide system according to claim 21, wherein the length of the arm extending between the arm-base connection and the needle guide is adjustable.

23. The needle guide system according to claim 21, wherein the connector is adjustable to secure the base to imaging devices having a plurality of shapes or sizes.

24. The needle guide system according to claim 21, wherein the arm is removably connected to the base.

25. The needle guide system according to claim 21, wherein the needle guide is removably connected to the arm.

26. The needle guide system according to claim 21, wherein the needle guide is provided with a plurality of guide holes adapted to receive needles of different sizes.

27. The needle guide system according to claim 21, wherein the arm is provided with a longitudinally extending arm slot.

28. The needle guide system according to claim 27, wherein the base comprises a base pin arranged in the slot, and wherein the arm is adapted to pivot and slide with respect to the base.

29. The needle guide system according to claim 28, wherein the base pin is arranged in a longitudinal slot formed between two base walls of the base.

30. The needle guide system according to claim 21, wherein the needle guide comprises a needle guide pin, and wherein the arm is adapted to pivot on the pin.

* * * * *